United States Patent [19]
Goetz

[11] Patent Number: 5,631,282
[45] Date of Patent: May 20, 1997

[54] TRITERPENES

[75] Inventor: Michael A. Goetz, Scotch Plains, N.J.

[73] Assignee: Merck & Co., Inc., Rahway, N.J.

[21] Appl. No.: 476,806

[22] Filed: Jun. 7, 1995

[51] Int. Cl.[6] ............... C07D 493/02; A61K 31/365
[52] U.S. Cl. ........................... 514/450; 549/268
[58] Field of Search ..................... 549/268; 514/450

[56] References Cited

PUBLICATIONS

Abrue, H.D.S., Fo, R.B., Gottlieb, H.E., Shoolery, J.N. "A Nor–Triterpenoid from Lophanthera Lactescens", Phytochemistry, 29(7), 2257–2261 (1990). 1990.

Sabata, B., Connolly, J.D., Labbe, C., Rycroft, D.S. "Tetrenortriterpenoids and Related Substances. Part 19. Revised Structures of Atalantolide and Atalantin, Limonoids from the Root Bark of Atalantia monophylla Correa (Rutaceae)", J. Chem. Soc. Per 1977.

Primary Examiner—C. Warren Ivy
Assistant Examiner—Lyman H. Smith
Attorney, Agent, or Firm—Valerie J. Camara; Mark R. Daniel

[57] ABSTRACT

Four triterpenes of Formula 1 (where "---" is either a single or double bond and R is H or acetate) are disclosed which are potent and selective immunosuppressive agents. These compounds have been isolated from *Spachea correa* root.

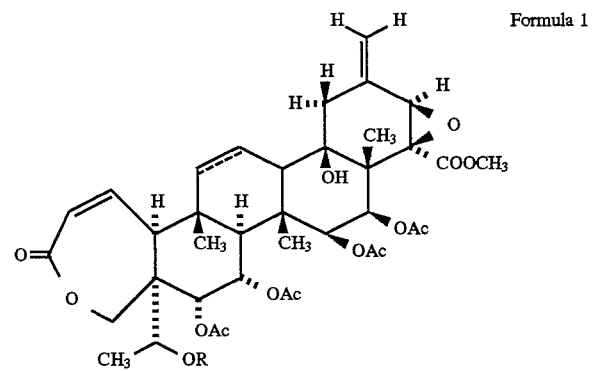

12 Claims, 4 Drawing Sheets

TRITERPENES

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma.

Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A (CsA), which was approved by the US FDA in 1983 is currently the leading drug used to prevent rejection of transplanted organs. In 1993, FK-506 (Prograf) was approved by the US FDA for the prevention of rejection in liver transplantation. CsA and FK-506 act by inhibiting the body's immune system from mobilizing its vast arsenal of natural protecting agents to reject the transplant's foreign protein. In 1994, CsA was approved by the US FDA for the treatment of severe psoriasis and has been approved by European regulatory agencies for the treatment of atopic dermatitis. Though they are effective in fighting transplant rejection, CsA and FK-506 are known to cause undesirable side effects including nephrotoxicity, neurotoxicity, and gastroinntestinal discomfort.

Four active components of *Spachea correa* have now been identified which inhibit thymidine uptake of T cells and are useful as immunosuppressent agents in animals, including man.

SUMMARY OF THE INVENTION

This invention is concerned with compounds of structural Formula 1, where "---" represents either the presence or absence of a double bond.

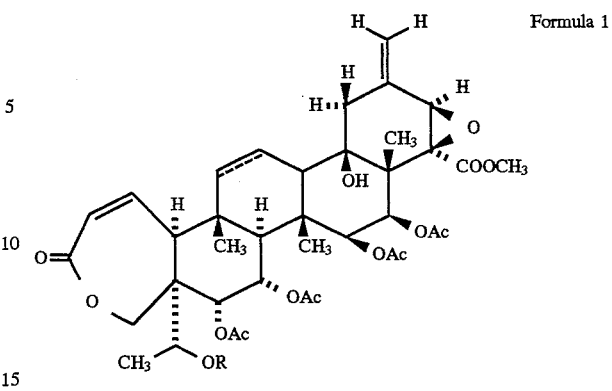

Formula 1 where R is H or Ac.

These compounds are useful as immunosuppressent agents in animals including man.

This invention is also concerned with the process of obtaining these compounds from the root of *Spachea correa*; pharmaceutical formulations comprising one or more of the compounds as an active immunosuppressent either alone or in combination with other agents which exhibit immunosuppressant capabilities; and a method of providing immunosuppression to prevent rejection of transplanted organs by administering one or all of these compounds or formulations thereof to a patient in need of such treatment.

Figure 1:
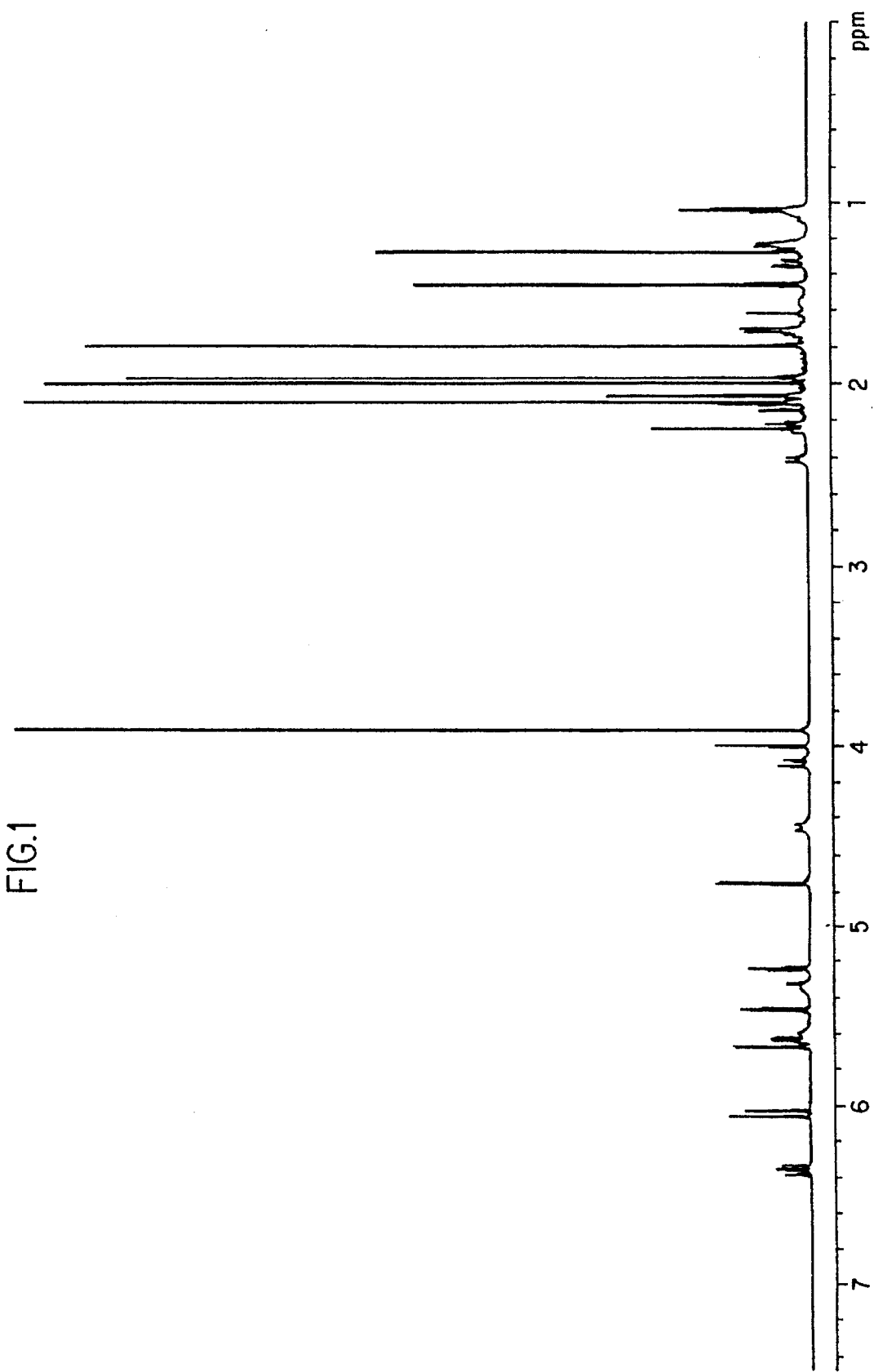
FIG. 1 is the $^1$H NMR spectrum of Compound 1(a).
Figure 2:
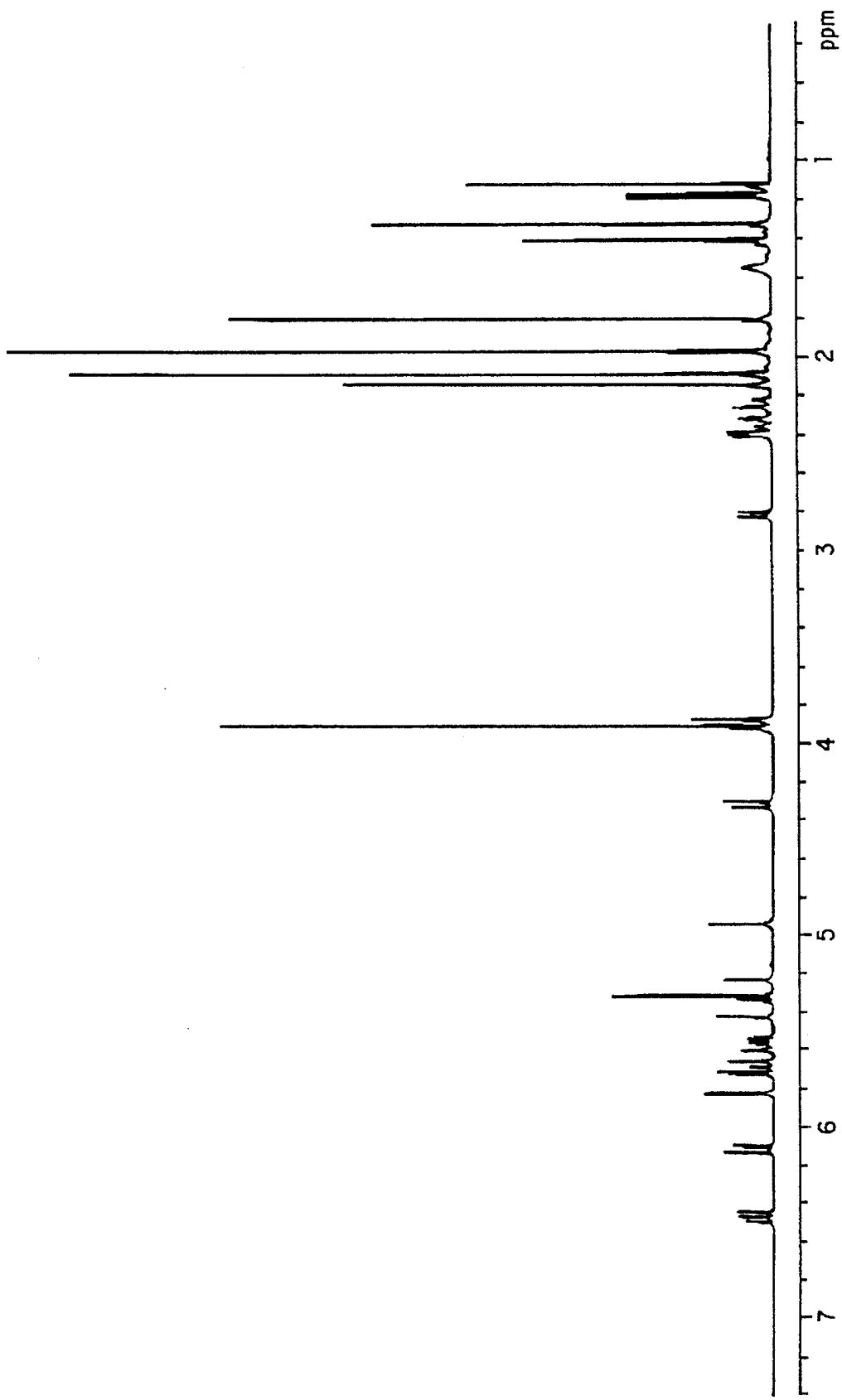
FIG. 2 is the $^1$H NMR spectrum of Compound 1(b).

All $^1$H NMR spectra were recorded at 400 MHz in $CD_2Cl_2$ on a Varian Unity 400 NMR spectrometer at 25° C. Chemical shifts are in ppm relative to TMS at zero ppm using the solvent peak at δ5.32 as internal standard.

DETAILED DESCRIPTION OF THE INVENTION

This invention is concerned with compounds of structural Formula 1(a) and 1(b), 1(c), 1(d) or pharmaceutically acceptable salts thereof.

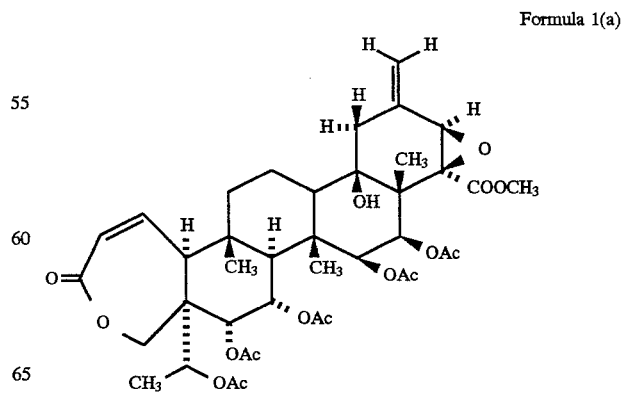

Formula 1(a)

Formula 1(b)

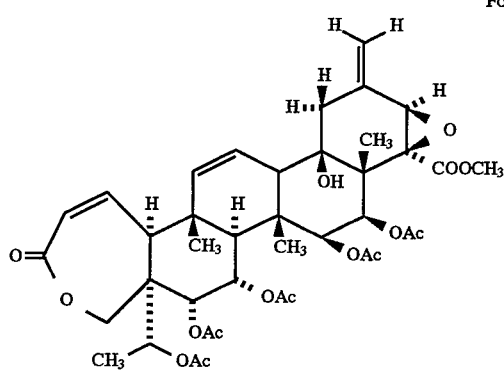

Formula 1(c)

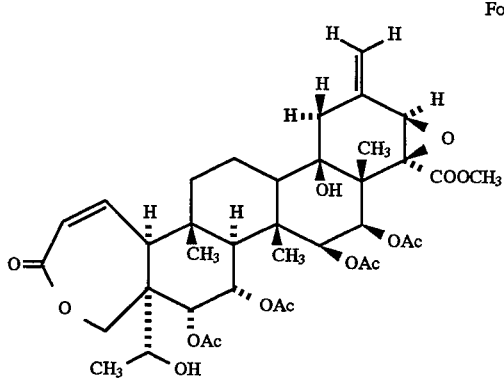

Formula 1(d)

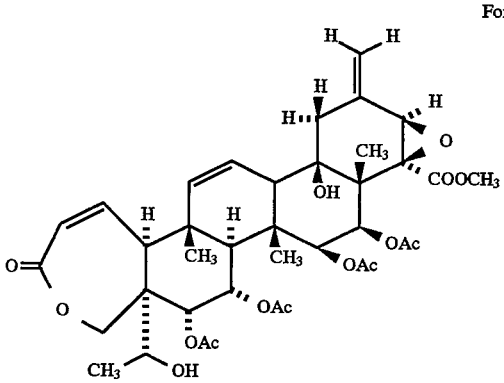

These compounds are useful as immunosuppressent agents in animals including man.

A compound similar to that of Formula 1(a) is known from the Brazilian plant Lophanthera lactescens, however, no biological activity has been reported before this disclosure. The novel Δ-11,12 analog which is herein called the "compound of Formula 1(b)" as well as the compounds labeled Formula 1(c) and Formula 1(d) have not been previously disclosed. All four compounds have been isolated from the ethanol extract of root from Spachea correa.

This invention is also concerned with the process of obtaining these compounds from the root of Spachea correa. This process is exemplified in the Examples.

The compounds of the present invention have the pharmacological properties required for immunosuppressents, namely the ability to suppress T cell proliferation.

All pharmaceutically active crystal forms, hydrates, solyates, and other morphological forms of these compounds are considered within the scope of this invention.

In the novel method of this invention of inducing immunosuppression, one or all of the compounds of this invention, or their pharmaceutically acceptable salts, is administered in an amount ranging from about 0.0001 to about 20 mg per kg of body weight per day, preferably from about 0.001 to about 10 mg per kg of body weight per day in a single dose or in 2 to 4 divided doses or by continuous intravenous infusion.

The compounds of this invention can be administered as the sole active ingredient or in combination with other immunosuppressent agents or other treatment as needed.

The compounds, or pharmaceutically acceptable salts thereof, of the present invention, in the described dosages, are administered orally, intraperitoneally, subcutaneously, intramuscularly, transdermally, sublingually or intravenously. The compounds are preferably administered orally for example in the form of tablets, troches, capsules, elixirs, suspensions, syrups, wafers, chewing gum or the like prepared by art recognized procedures. Another preferable means of introducing this medication is in an intravenous solution or suspension, for example in the form of a solution in 10% cremophor and 5% dimethylsulfoxide which is diluted with saline prior to use.

While the compounds of this invention may be administered either alone or together, they may also be administered, either alone or together with comprising an antiproliferative agent selected from the group consisting of: azathioprine, brequinar sodium, deoxyspergualin, mizaribine, mycophenolic acid morpholino ester, cyclosporin, FK-506 and rapamycin, or other compounds which would be co-administered to provide immunosupression.

Due to the ability of the compounds of Formula 1(a), 1(b), 1(c) and 1(d) to act as immunosuppressents, these compounds may be useful in preventing or treating graft-versus-host diseases, autoimmune disease, inflammatory, proliferative and hyper-proliferative skin diseases and cutaneous manifestations of immunologically-mediated illnesses, male or female pattern alopecia or alopecia senilis, respiratory diseases, hepatic injury associated with ischemia, eye diseases, intimation of mucosa or blood vessels, intestinal lesions associated with thermal burns, cyto-megalovirus infection, renal disease, bone disease, circulatory disease, periodontal disease, nephrotic syndrome, hemolytic-uremic syndrome, muscular dystrophy, intestinal inflammations/allergies and hepatic disease through administration of either or all of these compounds to a patient in need thereof.

EXAMPLE 1

A Method of Extracting the Compounds of Formula 1(a) and 1(b) from Spachea correa.

One gram of an ethanol extract of the roots of Spachea correa was partitioned between 100 ml of hexane (twice) and 100 ml of 90% aqueous methanol. After separation of the phases, the defatted methanol was concentrated down under vacuum to give an aqueous suspension. This was diluted out to 100 ml with water and extracted, with 100 ml of methylene chloride.

The bioactive methylene chloride extract was dried down to give 12 mg of residue. This was first fractionated by preparative thin layer chromatography (TLC) on a 20 cm by 20 cm E. Merck silica gel 60$F_{254}$ plate of 1 mm thickness using methylene chloride—ethyl acetate 1:1 (v/v) as solvent, then by high performance liquid chromatography (HPLC) using a Zorbax RxC$_8$ 4.6 mm×25 cm column, operated at 50° C. and eluted with a 50 minute gradient of acetonitrile:water (1:1, v/v) to 100% acetonitrile, delivered at 1 ml/min, to afford 4 mg of compound 1(a) and 1 mg of 1(b).

Homogeneity of the preparations was ascertained in several TLC systems, such as E. Merck silica gel 60$F_{254}$, methylene chloride-ethyl acetate 1:1, Rf 1(a) 0.4, Rf 1(b)

0.3; Whatman $KC_{18}$, methanol-water 9:1, Rf 1(a) 0.65, Rf 1(b) 0.75 and by HPLC using a Zorbax $RxC_8$ column, acetonitrile-water 3:2, k' 1(a) 4.15, k' 1(b) 3.30; and by NMR.

Mass spectra were recorded on JEOL SX-102A (electron impact, EI,903V) and JEOL HX1 110 (Fast Atom Bombardment, FAB) mass spectrometers. Exact mass measurements were performed at high resolution (HR-EI) using perfluorokerosene (PFK) as the internal standard. Trimethylsilyl derivatives were prepared with a 1:1 mixture of BSTFA-pyridine at room temperature The FAB spectrum was mn in a matrix of dithiothreitol dithioerthritol (20/80).

The compound of Formula 1(a) runs underivatized by EI. The molecular ion is observed a m/z 788 and three successive loses of acetic acid are observed. The base peak is observed a m/z 334. The compound does not silylate. Scanning HR-EI indicated a molecular formula of $C_{40}H_{52}O_{16}$. A table of the critical HR-EI data is given below.

| Observed m/z | Formula | Assignment |
| --- | --- | --- |
| 788.3220 | $C_{40}H_{52}O_{16}$ | M+ |
| 728.3040 | $C_{38}H_{48}O_{14}$ | M-acetic acid |
| 668.2834 | $C_{36}H_{44}O_{12}$ | M-2 x acetic acid |
| 334.1417 | $C_{18}H_{22}O_6$ | base peak |

$^{13}C$ NMR spectra were recorded for the compound of Formula 1(a) in $CD_2CL_2$ at 100 MHz on a Varian Unity 400 NMR spectrometer at 20° C. Chemical shifts are given in ppm relative to tetramethylsilane (TMS) at zero ppm using the solvent peak at 53.8 ppm as internal standard. The following data were observed: 15.0, 15.2, 16.8, 17.1, 20.7*, 20.9, 21.1, 21.6, 21.8, 22.2, 35.6, 40.8*, 42.1, 43.6, 45.1, 47.5, 49.3*, 53.5, 59.1, 62.6, 63.5, 66.1, 66.7*, 68.4*, 69.9, 73.9, 75.0, 75.6, 77.1*, 119.4, 123.7, 138.9, 143.0, 167.7, 169.2, 169.3*, 170.25, 170.31, 170.8, 171.3 ppm (where the * signifies the observation as broad resonances). The carbon count of 40 is in agreement with the molecular formula $C_{40}H_{52}O_{16}$ derived by scanning HR EI-MS.

The $^1H$ NMR. spectra of compound of Formula(a) is provided as FIG. 1. The spectra was recorded at 400 MHz in $CD_2Cl_2$ on a Varian Unity 400 NMR spectrometer at 25° C. Chemical shifts are in ppm relative to TMS at zero ppm using the solvent peak at δ5.32 as the internal standard.

The mass spectra of the compound of Formula 1(b) was obtained as above. The following results were obtained.

| Observed m/z | Formula | Assignment |
| --- | --- | --- |
| 786.3075 | $C_{40}H_{50}O_{16}$ | M+ |
| 726.2886 | $C_{38}H_{46}O_{14}$ | M-acetic acid |
| 666.2651 | $C_{36}H_{42}O_{12}$ | M-2 x acetic acid |
| 606.2451 | $C_{34}H_{38}O_{10}$ | M-3 x acetic acid |
| 489.2099 | $C_{26}H_{33}O_9$ | base peak |
| 471.1992 | $C_{26}H_{31}O_8$ | |

$^{13}C$ NMR spectra were recorded for the compound of Formula(b) using the procedure described above. The following results were observed: 14.8, 14.9, 17.3, 20.8, 20.9, 21.3, 21.7, 21.8, 21.9, 27.1, 35.1, 40.6, 42.3, 45.4, 48.1, 50.4, 53.5, 54.1, 57.8, 63.7, 66.2, 67.8, 68.6, 71.4, 73.3, 73.8, 74.4, 119.5, 121.1, 124.3, 137.1, 138.9, 143.3, 167.6, 168.6, 169.3, 169.5, 169.9, 171.0, 171.7 ppm.

The carbon count of 40 is in agreement with the molecular formula $C_{40}H_{50}O_{16}$ derived by scanning HR EI-MS.

Figure 3:
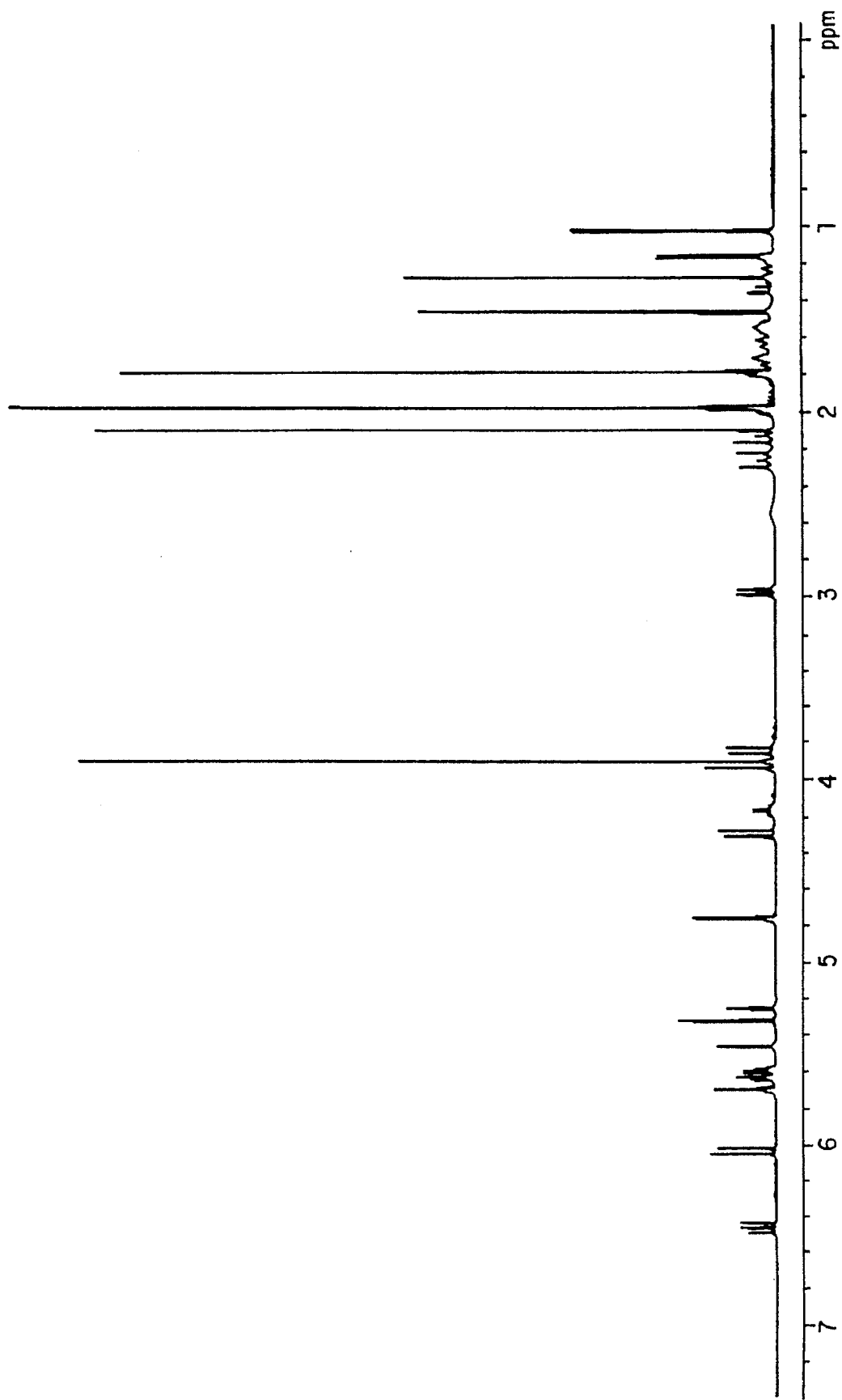
FIG. 3 is the $^1$H NMR spectrum of Compound 1(c).

The $^1H$ NMR spectra of the compound of Formula 1(b) is provided as FIG. 3. The spectra was recorded in the manner previously described.

EXAMPLE 2

A Method of Extracting the Compounds of Formula 1(C) and 1(D) from *Spachea correa*.

Analogs of the compounds of Formula 1(a) and 1(b) could be detected in the crude extract and fractions thereof when the process of Example 1 was carried out on a larger scale. Thus, 50 g of ethanol extract were partitioned as described in Example 1 using 900 ml of each solvent at each step.

Partial purification of the methylene chloride extract was achieved by column chromatography on E. Merck silica gel 60 (120 ml), eluting with a step gradient of ethyl acetate in methylene chloride. The step gradient was designed so that the column was washed first with 100% methylene chloride and then with methylene chloride-ethyl acetate mixtures of 9:1, 8:2, 3:2, 2:1, 1:1, 1:2, 2:8 and 1:9. Ultimately the column was washed with 100% ethyl acetate. Fractions eluted with methylene chloride-ethyl acetate 3:2 were enriched in compound of Formula 1(a) and 1(b). These were resolved by HPLC using a Zorbax $RxC_8$ 9 mm×25 cm column, maintained at 50° C. and eluted at 4 ml/min with acetonitrile-water 1:1 v/v. Three identical runs finally afforded 100 mg and 20 mg respectively of 1(a) and 1(b) after crystallization from methanol. Later-eluting fractions from the silica gel column above were found to contain at least two related compounds based on UV spectra and color reactions on TLC plates. Material from the methylene chloride-ethyl actate 1:1 and 1:2 washings were combined and evaporated down. Separation was achieved on the same HPLC column as above, eluting with a 50 minute gradient of 30% to 50% acetonitrile in water. Two identical runs gave 6 mg of purified compound 1(c). Fractions containing the compound of Formula 1(d) were again processed by HPLC (same column) using acetonitrile-water 3:7 delivered isocratically, to yield 2 mg of purified Formula 1(d).

The mass spectra of these compounds were recorded on a Finnigan TSQ700 mass spectrometer (electrospray ionization, ESI). The samples were analyzed by LC/MS using a 2.1×150 mm $C_8$ column at 0.2 ml/min. with a mobile phase of 45% acetonitrile/0.01M aqueous ammonium acetate at 50° C. Component 1(d) had a retention time of 10.5 min. and a molecular weight of 744 which is observed a m/z: 745 (M+H), 762 (M+$NH_3$), 786 (M+H+MeCN). Component 1(c) has a retention time of 11.8 and a molecular weight of 746 which is observed at m/z: 747 (M+H), 764 (M+$NH_3$) and 788 (M+H+MeCN).

The $^{13}C$ NMR spectra obtained for the compound of Formula 1(c) using the conditions previously described is as follows: 15.1 (2×), 16.9, 19.8, 20.8, 20.91, 20.94, 21.9, 22.3, 35.6, 40.6, 42.2, 43.9, 45.0, 47.7, 50.8, 53.5, 55.6, 61.8, 63.5, 66.0, 67.6 (2×), 69.8, 70.0, 73.9, 75.0, 75.6, 119.3, 123.7, 139.0, 144.4, 167.8, 169.2, 169.5, 170.1, 170.4, 171.4 ppm.

The carbon count of 38 is in agreement with the molecular formula $C_{38}H_{50}O_{16}$ derived by scanning HR EI-MS.

Figure 4:
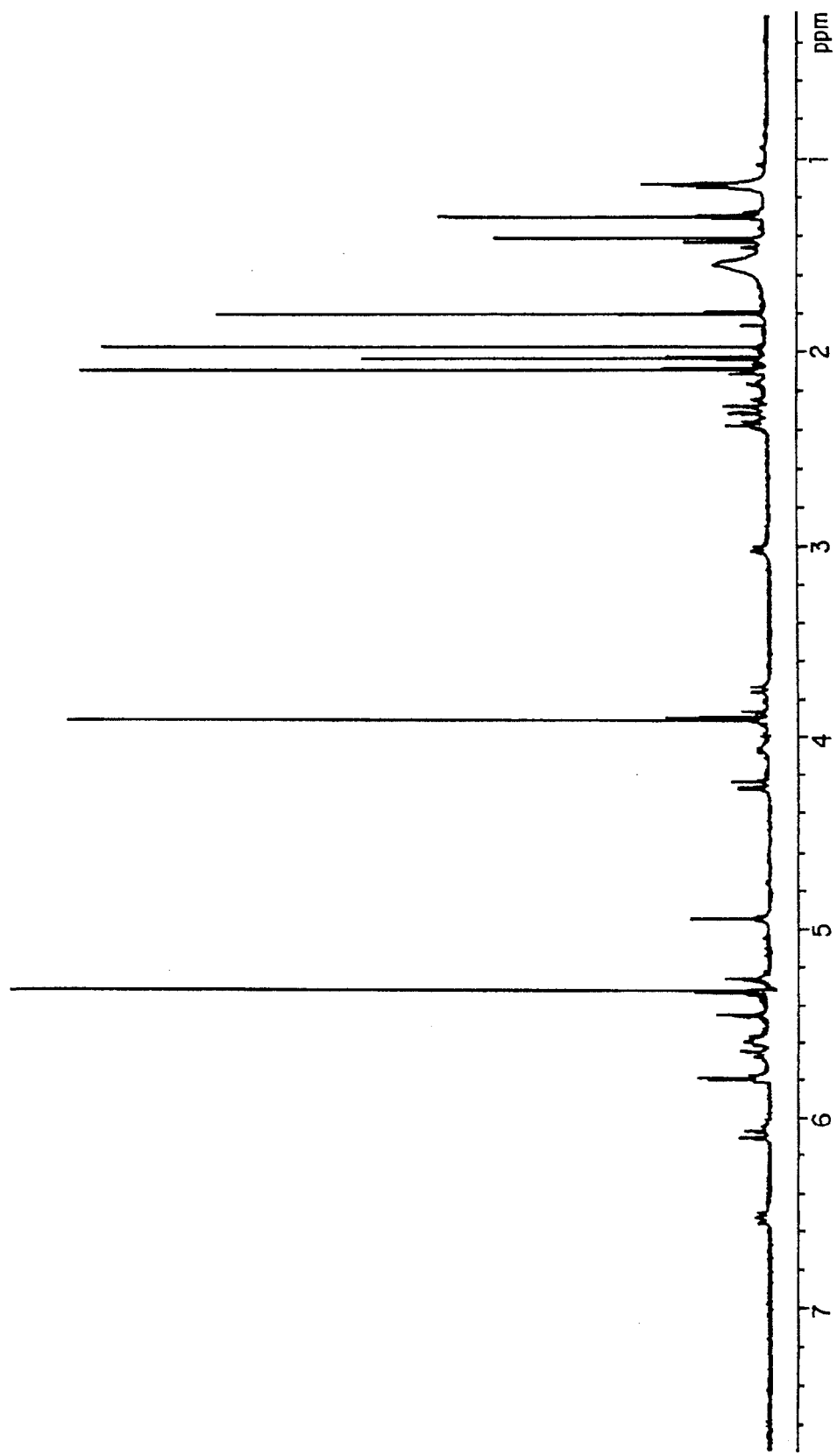
FIG. 4 is the $^1$H NMR spectrum of Compound 1(d).

$^1H$ NMR spectra for the compound of Formula 1(c) is shown in FIG. 3 and for the compound of Formula 1(d) in FIG. 4.

EXAMPLE 3

Separation by HPLC

Compounds of this invention were characterized by the following behavior during HPLC separation on a Zorbax $RxC_8$ 4.6 mm×25 cm column, maintained at 50° C. and eluted at 1 ml/min with acetonitrile-water 3:2 v/v): Compound 1(a):k'=4.15; 1(b): k'=3.30; 1(c): k'=2.30; 1(d): k'=2.10.

Analyses using this HPLC system can be used to quantify the compounds in the crude extract or other mixtures, by comparing the absorbance of HPLC peaks at a wavelength of 220 nm with that produced by injections of known (weighed) amounts of pure standards.

EXAMPLE 4

Additional Purification Procedure

A simplified purification process allows for rapid fractionation of even larger amounts of crude extract and the preparation of gram amounts of the compounds of Formula 1(a) and 1(b).

The ethanol extract is first dissolved at 20 grams per 150 ml in methanol. This solution is diluted with 150 ml of water and then extracted three times with methylene chloride using 150 ml of methylene chloride each time. The pooled methylene chloride extracts are evaporated down and fractionation proceeds by repeated column chromatography on silica gel. One employs methylene chloridemethanol 97:3 in a first step; the mixed compounds of Formula 1(a) and 1(b) thus obtained are resolved by chromatographing on fresh silica gel eluted with methylene chloride-ethyl acetate 3:1. Volume of elution for the compound of Formula 1(a) ranges from about 2 to about 3.5 column volumes of solvent; that for the compound of Formula 1(b) is about 3 to about 4.5 column volumes. Finally, advantage is taken of the low solubility of these compounds, and, after total resolution by chromatography, the compounds of Formula 1(a) and 1(b) can be precipitated and or crystallized from concentrated methanol solutions.

EXAMPLE 5

T Cell IL-2 Assay

Peripheral blood mononuclear cells from healthy donors were separated by density centrifugation with ficoll-hypaque (LSM, Organon Teknika, Durham, N.C.), followed by resetting with neuraminidase treated SRBC. After another centrifugation with LSM, the SRBC of the rosetted T cells were then lysed with ammonium chloride lysing buffer (GIBCO). Such purified T cells were resuspended at $3\times10^6$/ml in RPMI 1640 culture medium (GIBCO, Grand Island, N.Y.) supplemented with 10% fetal calf serum (HyClone Laboratories, Logan, Utah), 100 mM glutmine, 1 mM sodium pyruvate, 0.1 mM non-essential amino acids, and 1% penn-strep (GIBCO). The cell suspension was immediately distributed into 96 well round-bottom microculture plates (Costar) at 200 ul/well. The various dilutions of test compound were then added in triplicate wells at 25 ul/well, incubated for 15 min at 37° C. Ionomycin (125 ng/ml), anti-CD28 (100 ng/ml) and PMA (1 or 5 ng/ml, with ionomycin or anti-CD28, respectively) were added to the appropriate wells. The culture plates were then incubated at 37° C. in a humidified atmosphere of 5% $CO_2$–95% air for 24 hours. The supernatants were removed, and assayed for IL-2 with an IL-2 ELISA Kit (Collaborative Biomedical Products, Bedford. Mass.). Mean OD and units of IL-2 of the replicate wells were calculated and the results were expressed as concentration of compound required to inhibit IL-2 production of T cells by 50%. The compounds of Formula 1(a), 1(b), 1(c) and 1(d) all block IL-2 secretion at concentrations of 10 uM or less. That is, these compounds are all immunosuppressent agents.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of Formula 1

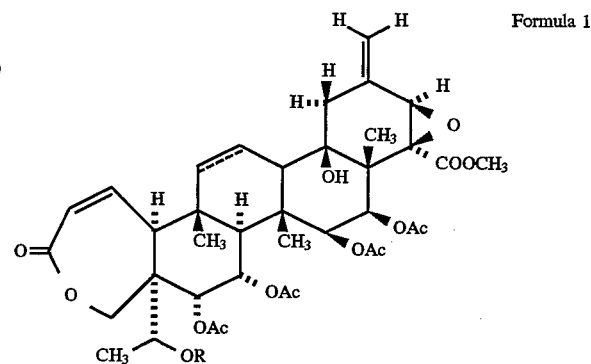

Formula 1 where '---' represents either the presence or absence of a double bond when R is H and '---' represents the presence of a double bond when R is Ac; or a pharmaceutically acceptable salt, hydrate or crystal form thereof.

2. A method of suppressing the immune system in a subject in need thereof, which comprises the administration to the subject of an immune suppressing amount of a compound selected from Formula 1(a), 1(b), 1(c), or 1(d)

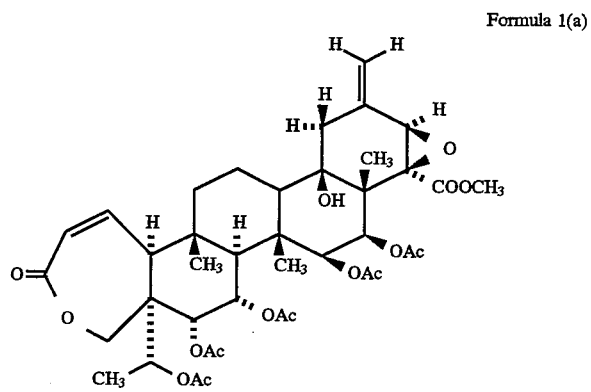

Formula 1(a)

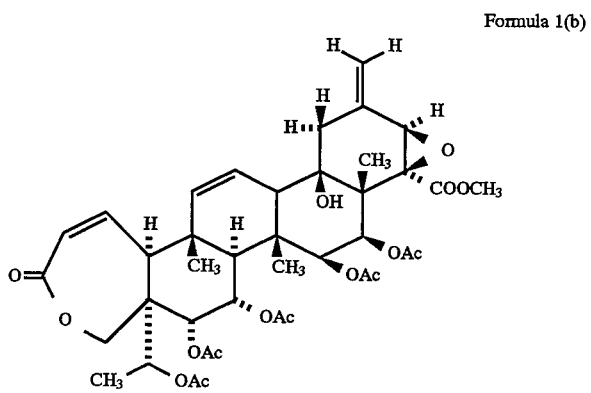

Formula 1(b)

Formula 1(c)

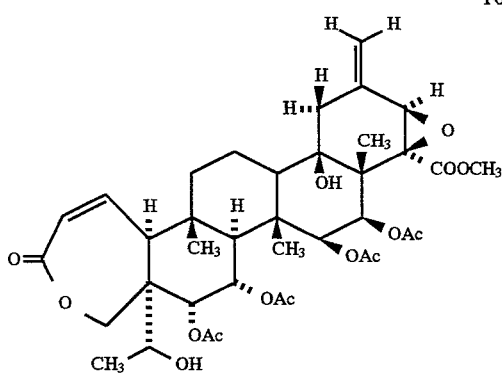

Formula 1(d)

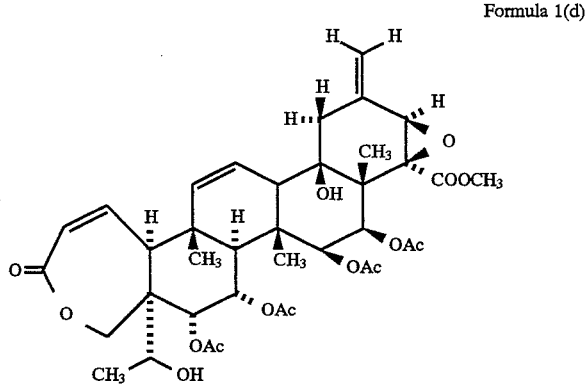

a pharmaceutically acceptable hydrate or crystal form thereof.

3. The method of claim 2, wherein the compound has the following formula:

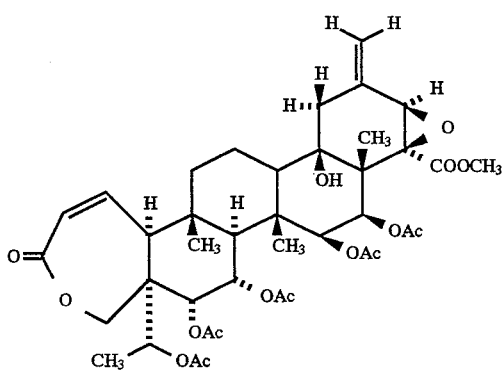

or a pharmaceutically acceptable salt, hydrate or crystal form thereof.

4. The method of claim 2, wherein the compound has the following formula:

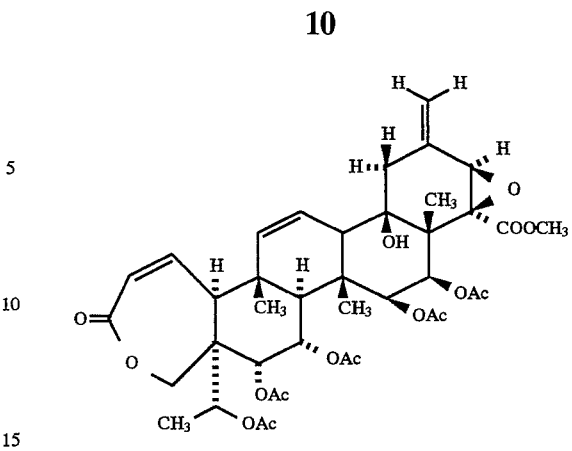

or a pharmaceutically acceptable salt, hydrate or crystal form thereof.

5. The method of claim 2, wherein the compound has the following formula:

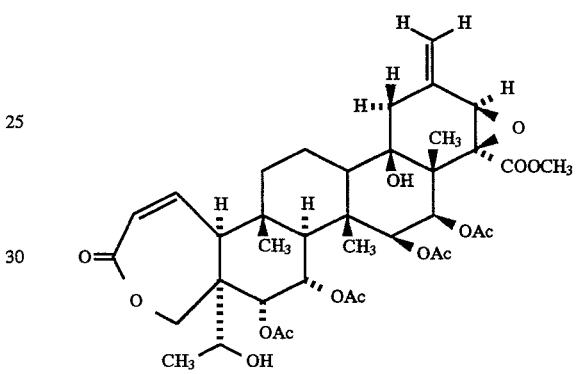

or a pharmaceutically acceptable salt, hydrate or crystal form thereof.

6. The method of claim 2, wherein the compound has the following formula:

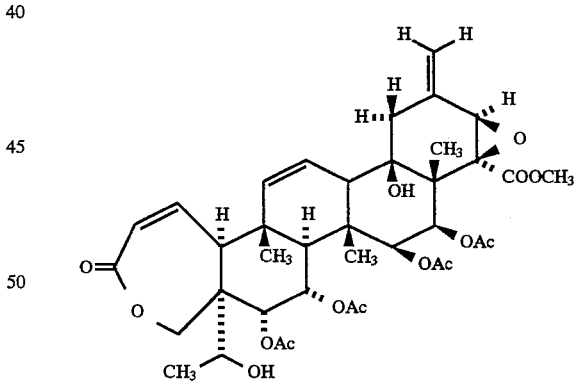

or a pharmaceutically acceptable salt, hydrate or crystal form thereof.

7. A pharmaceutical formulation comprising a pharmaceutically acceptable carrier and a therapeutically effective amount of the compound of Formula 1(a), 1(b), 1(c) or 1(d) of claim 2 or a pharmaceutically acceptable crystal form or hydrate thereof.

8. The pharmaceutical formulation of claim 7, comprising in addition, an antiproliferative agent selected from the group consisting of: azathioprine, brequinar sodium, deoxyspergualin, mizaribine, mycophenolic acid morpholino ester, cyclospofin, FK-506 and rapamycin.

9. The method of claim 2, comprising the concomitant administration of an antiproliferative agent.

10. A method of preventing or treating the resistance to transplantation or transplantation rejection of organs or tissues into a patient in need thereof, which comprises the administration of a compound of Formula 1(a), 1(b), 1(c) or 1(d) of claim 2.

11. A method of extracting the compounds of Formula 1(a), 1(b), 1(c) or 1(d) of claim 2 from *Spachea correa* comprising the steps of:

(a) extracting the roots of *Spachea correa* with ethanol;
   (b) extracting an aliquot of the ethanol extract of (a) with a mixture of hexane and 90% aqueous methanol.

12. A method of separating the compounds compounds of Formula 1(a), 1(b), 1(c) or 1(d) of claim 2 from an ethanol extract of the root of *Spachea correa* comprising the steps of:

(a) extracting the roots of *Spachea correa* with ethanol;
   (b) extracting an aliquot of the ethanol extract of (a) with a mixture of hexane and 90% aqueous methanol;
   (c) removing the methanol phase and concentrating the methanol phase under vacuum until an aqueous suspension is produced;
   (d) diluting the aqueous suspension of (c) with water to produce an aqueous solution;
   (e) extracting the aqueous solution of (d) with methylene chloride;
   (f) chromatographing the methylene chloride extract of (e) on silica gel using a step gradient of ethyl acetate in methylene chloride for elution wherein the steps comprise the use of 100% methylene chloride, followed by combinations of methylene chloride—ethyl acetate mixtures ranging from 9:1 to 100% ethyl acetate but including at least 3:2, 1:1 and 1:2 methylene chloride—ethyl acetate mixtures;
   (g) collecting the fraction with a methylene chloride—ethyl acetate ration of about 3:2 which contains the compounds of Formula 1(a) and 1(b);
   (h) resolving the compounds of Formula 1(a) and 1(b) from the fraction of (g) by HPLC;
   (i) collecting the fraction with a methylene chloride—ethyl acetate ratio of about 1:1 and 1:2 which contains the compounds of Formula 1(c) and 1(d);
   (j) separating the compounds of Formula 1(c) and 1(d) by HPLC.

* * * * *